United States Patent
Dakka et al.

(10) Patent No.: US 7,253,330 B2
(45) Date of Patent: *Aug. 7, 2007

(54) OLIGOMERIZATION PROCESS

(75) Inventors: Jihad Mohammed Dakka, Whitehouse Station, NJ (US); Hans K. T. Goris, Laakdal (BE); Georges M. K. Mathys, Bierbeek (BE); Stephen Harold Brown, Brussels (BE); Bruce R. Cook, Stewartsville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 282 days.

This patent is subject to a terminal disclaimer.

(21) Appl. No.: 10/425,430

(22) Filed: Apr. 29, 2003

(65) Prior Publication Data

US 2004/0220440 A1    Nov. 4, 2004

(51) Int. Cl.
C07C 2/02 (2006.01)
C07C 1/00 (2006.01)

(52) U.S. Cl. .................. 585/533; 585/324; 585/502; 585/518; 585/520; 585/530

(58) Field of Classification Search .............. 585/520, 585/531, 533, 530, 502, 324, 518
See application file for complete search history.

(56) References Cited

U.S. PATENT DOCUMENTS

| | | | |
|---|---|---|---|
| 3,960,978 A | 6/1976 | Givens et al. | 260/683.15 R |
| 4,016,218 A | 4/1977 | Haag et al. | 260/671 R |
| 4,021,502 A | 5/1977 | Plank et al. | 260/683.15 R |
| 4,556,477 A | 12/1985 | Dwyer | 208/111 |
| 5,157,201 A | 10/1992 | Norris | 585/820 |
| 6,884,916 B1 * | 4/2005 | Brown et al. | 585/530 |
| 2002/0111523 A1 | 8/2002 | Mathys et al. | |

FOREIGN PATENT DOCUMENTS

| EP | 0 746 538 B1 | 12/1996 |
|---|---|---|
| WO | 93/16020 * | 8/1993 |
| WO | 93/25475 A1 | 12/1993 |
| WO | 01/30941 A1 | 5/2001 |

* cited by examiner

Primary Examiner—Glenn Caldarola
Assistant Examiner—In Suk Bullock
(74) Attorney, Agent, or Firm—Andrew B. Griffis

(57) ABSTRACT

In a process for oligomerizing an olefinic hydrocarbon feedstock comprising sulfur-containing molecules, the feedstock is contacted in the absence of hydrogen with a first metal oxide catalyst at a temperature in excess of 150° C. and then is contacted under olefin oligomerization conditions with a second catalyst comprising a crystalline molecular sieve, such as ZSM-22 or ZSM-57.

22 Claims, 1 Drawing Sheet

OLIGOMERIZATION PROCESS

FIELD

The present invention relates to a process for the manufacture of higher molecular weight organic molecules from lower molecular weight materials, especially olefins, by oligomerization.

BACKGROUND

It is known to oligomerize lower olefins, particularly $C_2$ to $C_6$ olefins, to produce higher molecular weight olefinic products useful as, for example, fuels and precursors in the production of plasticizers, surfactants, and freeze point depressants for lubricating oils. Typically, known oligomerization processes involve contacting a lower olefin with a solid acid catalyst, such as phosphoric acid or, more recently, a crystalline molecular sieve.

For example, U.S. Pat. Nos. 3,960,978 and 4,021,502 disclose the conversion of gaseous olefins in the range of ethylene to pentene, either alone or in admixture with paraffins, into an olefinic gasoline blending stock by contacting the olefins with a ZSM-5 type zeolite. In addition, EP-B-746,538 discloses oligomerization of propene and butene to produce enhanced yields of the trimer using zeolites of the structure types MFI, TON, and MFS, such as ZSM-5, ZSM-22 and ZSM-57.

It is, however, found that commercially available olefinic feedstocks cause rapid deactivation of existing oligomerization catalysts and give a lower selectivity to the trimer than might be expected from the disclosure of EP-B-746,538. Although the reason for these observations is not fully understood, it is believed that the presence of certain sulfur compounds is at least partly responsible for the decrease in activity and selectivity. In particular, it is believed that low molecular weight, aliphatic thiols, sulphides and disulphides are especially troublesome, for example dimethyl, diethyl, and ethyl methyl sulphides, n-propane thiol, 1-butane thiol and 1,1-methylethyl thiol, ethylmethyl and dimethyl disulphides, and tetrahydrothiophene. There is therefore a need for an oligomerization process which exhibits improved catalyst life when used with commercially available olefinic feedstocks.

U.S. Pat. No. 5,157,201 discloses a process for oligomerizing a sulfur-containing $C_2$-$C_4$ olefin feed over a phosphoric acid catalyst, in which the feed is initially passed through a bed of adsorbent at 50 to 175° C. and in the absence of added hydrogen. The adsorbent is at least one metal oxide selected from cobalt oxide, nickel oxide, molybdenum oxide, zinc oxide and copper oxide. The metal oxide is said to be effective in adsorbing 80 to 99% of the sulfur in the feed.

WO 01/30941 discloses an olefin oligomerization process in which a sulfur-containing olefinic hydrocarbon feedstock is contacted with a hydrotreating catalyst in the absence of hydrogen and in the liquid phase. The catalyst typically comprises mixed nickel and molybdenum oxides or mixed cobalt and molybdenum oxides on an alumina support. The catalyst oligomerizes the sulfur compounds as well as the olefins in the feedstock so that sulfur-containing feedstocks can be treated without the need for an initial adsorption step and without rapid reduction in catalyst activity.

According to the present invention, it has now been found that, by prior treatment with a metal oxide at a temperature in excess of 150° C., sulfur-contaminated olefinic feedstocks can be selectively oligomerized over molecular sieve catalysts with a marked increase in the lifetime of the oligomerization catalyst as compared to the same process without the pretreatment step.

SUMMARY

Accordingly, the invention resides in a process for oligomerizing an olefinic hydrocarbon feedstock comprising sulfur-containing molecules, the process comprising:
(a) contacting the feedstock in the absence of hydrogen with a first metal oxide catalyst at a temperature in excess of 150° C., and then
(b) contacting the feedstock from (a) under olefin oligomerization conditions with a second catalyst comprising a crystalline molecular sieve.

Conveniently, the hydrocarbon feedstock comprises at least one olefin having about 2 to about 12 carbon atoms, such as propylene and/or a butene.

Conveniently, the hydrocarbon feedstock comprises about 0.1 to about 10,000 ppm, such as about 1 to about 100 ppm, by volume of sulfur-containing molecules.

Conveniently, the sulfur-containing molecules are selected from methyl mercaptan, ethyl mercaptan, propyl mercaptan, dimethyl sulfide, diethyl sulfide, ethyl methyl sulphide, n-propyl sulfide, 1- and 2-propane thiol, 1-butane thiol and 1,1-methylethyl thiol, ethylmethyl disulphide, dimethyl disulphide and tetrahydrothiophene.

Conveniently, the metal oxide of the first catalyst is selected from nickel oxide, molybdenum oxide, mixtures thereof and sulfided versions of nickel oxide and/or molybdenum oxide.

Conveniently, the molecular sieve of the second catalyst has the TON or MFS structure type.

Conveniently, the feedstock is hydrated prior to contact with the second catalyst.

DETAILED DESCRIPTION OF THE EMBODIMENTS

Figure 1:
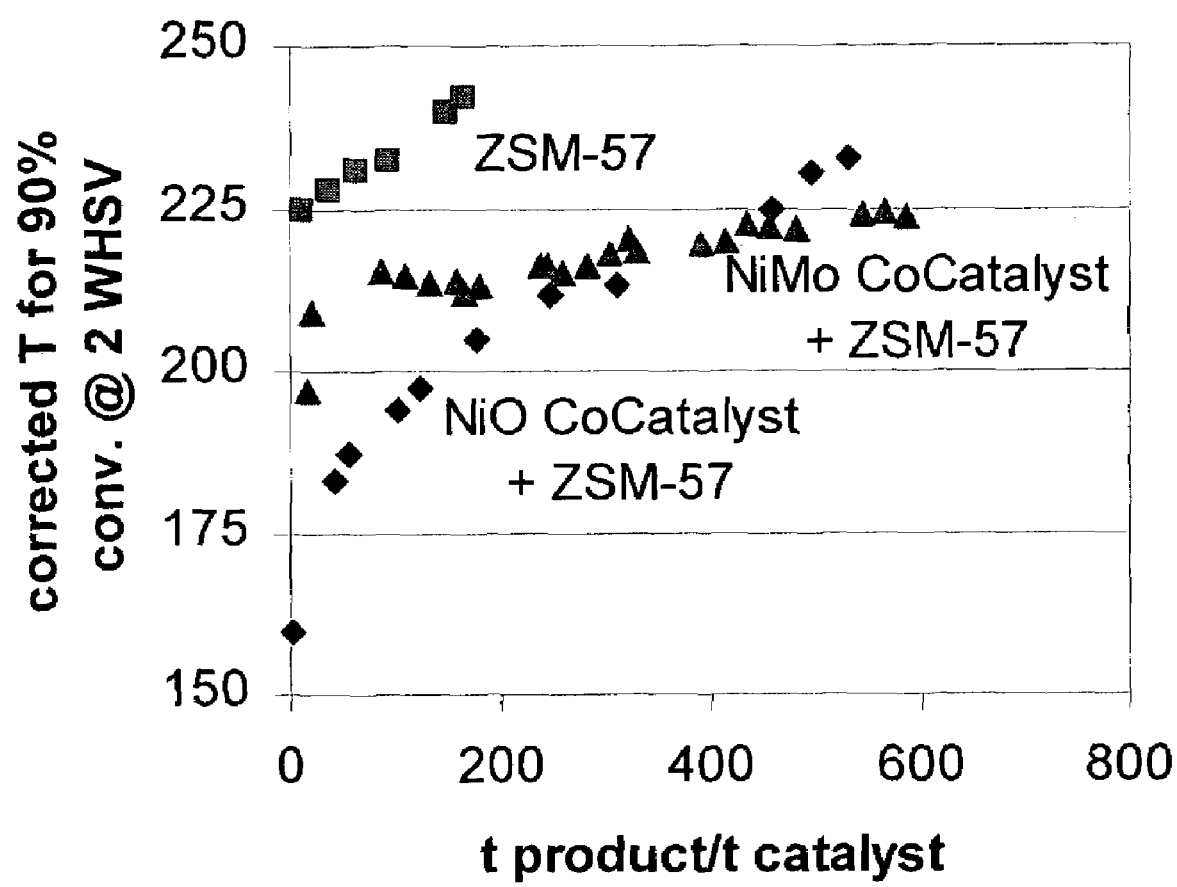
FIG. 1 is a graph showing the deactivation rate for a ZSM-57 catalyst used in the oligomerization of propylene both with and without a pretreatment step with a nickel oxide catalyst.

The present invention provides a process for oligomerizing a sulfur-containing olefinic hydrocarbon feedstock in which the feedstock is initially contacted in the absence of hydrogen with a first metal oxide catalyst at a temperature in excess of 150° C. The feedstock is then contacted under olefin oligomerization conditions with a second oligomerization catalyst comprising a crystalline molecular sieve. It is believed that the sulfur species in the feedstock which could poison the oligomerization catalyst are converted into non-poisonous compounds by the pretreatment with the metal oxide catalyst. As a result the rate of deactivation of the second oligomerization catalyst is significantly reduced as compared with a process which omits the pretreatment step.

It is to be appreciated that light olefin oligomerization is normally conducted using multiple, fixed bed reactors, which typically can run only a number of weeks before the catalyst deactivates and must be regenerated. When a catalyst requires regeneration, the reactor is shut down and feed flow is diverted to the remaining reactors on-line. Once catalyst activity has been restored, the reactor is brought back on-line. Substantial costs are involved in shutting down and regenerating reactors. Thus reducing the frequency of this activity by improving catalyst stability reduces unit operating costs.

Feedstock

The hydrocarbon feedstock used in the present process typically contains olefins having from about 2 to about 12 carbon atoms, such as from about 2 to about 6 carbon atoms. The feedstock itself may be or comprise an oligomer, such as a dimer, especially one provided by recycling a part of a product stream. In one embodiment, the feed contains propene, butenes, pentenes and/or hexenes. The process is especially applicable to propene and butene oligomerization.

Other suitable feedstocks include untreated refinery streams such as FCC, coker, and pygas streams as well as aromatics-containing streams, such as reformates.

In addition, the feedstock may comprise an inert diluent, for example, a saturated hydrocarbon.

As indicated above, the feedstock also includes sulphur-containing compounds, typically as impurities generated during production or separation of the feedstock. The feedstock may comprise from about 0.1 ppm to 10,000 ppm by volume of sulfur-containing compounds but more typically will contain from about 1 ppm to about 100 ppm, such as up to 50 ppm, for example up to 20 ppm by volume of such compounds. A typically encountered feedstock may have from 1 to 30 or from 2 to 20 ppm by volume of sulphur compounds, and the process is well suited to treating such feedstocks. The sulphur content is conveniently ascertained by gas chromatographic analysis using peak areas normalized with reference to a COS standard.

Examples of sulphur-containing compounds contained by the present feedstock include saturated aliphatic compounds, for example, thiols, sulphides, including cyclic sulphides, and disulphides. Typical compounds include, for example, methyl mercaptan, ethyl mercaptan, propyl mercaptan, dimethyl sulfide, diethyl sulfide, ethyl methyl sulphide, n-propyl sulfide, 1- and 2-propane thiol, 1-butane thiol and 1,1-methylethyl thiol, ethylmethyl disulphide, dimethyl disulphide and tetrahydrothiophene.

Metal Oxide Catalyst

The olefinic hydrocarbon feedstock is initially contacted with a metal oxide hydrotreating catalyst, which typically includes one or a combination of metal components from Groups VIA and VIIIA of the Periodic Table, such as nickel, cobalt, chromium, vanadium, molybdenum, tungsten, nickel-molybdenum, cobalt-nickel-molybdenum, cobalt-molybdenum, nickel-tungsten or nickel-tungsten-titanium. Generally, the metal component is selected for good hydrogen transfer activity and the catalyst as a whole should have good hydrogen transfer and minimal cracking characteristics. A preferred hydrotreating catalyst is a commercial NiMo/$Al_2O_3$ catalyst, such as HDN-60, manufactured by American Cyanamid. The catalyst may be used as it is received from the manufacturer, i.e., in its oxide form, or it may be presulfided. The support for the catalyst is conveniently a porous solid, usually alumina, or silica-alumina but other porous solids such as magnesia, titania or silica, either alone or mixed with alumina or silica-alumina may also be used.

The metal oxide catalyst may be provided in a separate bed or a separate reactor upstream of the oligomerization catalyst or may be provided as a top layer on the oligomerization catalyst.

Pretreatment Step

Pretreatment of the feedstock with the metal oxide catalyst is carried out at a temperature in excess of 150° C. and generally in excess of 175° C., such as from 180° C. to 260° C. Other conditions used in the pretreatment step normally include a weight hourly space velocity ranging from about 0.1 to about 100 $hr^{-1}$, such as from about 0.5 to about 10 $hr^{-1}$, and a pressure from about 400 psig to about 4000 psig (2860 to 27680 Kpaa), such as about 500 psig to about 1500 psig (3550 to 10440 kPaa).

The pretreatment is believed to convert the small sulfur-containing compounds in the feedstock to larger sulfur species which, by virtue of their size, have difficulty entering the pores of the molecular sieve oligomerization catalyst and thereby poisoning the catalyst. Although not fully understood, it is believed that the reaction can be attributed to more than one mechanism. Metal oxides, such as NiO are capable of stoichiometrically removing sulfur from the feed by sulfiding. The byproduct of this reaction is mostly olefins and water. The oxide catalyst can also convert sulfur-containing molecules via oligomerization to heavy sulfur compounds, which are believed to be too large to easily penetrate the pores of the zeolite catalyst reducing the deactivating effect. The oxide catalyst can also interconvert sulfides in the feed. For example, diethylsulfide is known to freely diffuse into ZSM-57 and poison active sites. However, NiO and NiMo catalysts can convert diethylsulfide into di-isopropylsulfide which is large enough to have difficulty diffusing into the ZSM-57 pores.

Molecular Sieve Oligomerization Catalyst

The oligomerization catalyst used in the present process can include any crystalline molecular sieve which is active in olefin oligomerization reactions. In one embodiment, the catalyst includes a medium pore size molecular sieve having a Constraint Index of about 1 to about 12. Constraint Index and a method of its determination are described in U.S. Pat. No. 4,016,218, which is incorporated herein by reference. Examples of suitable medium pore size molecular sieves include those of the TON structure type (for example, ZSM-22, ISI-1, Theta-1, Nu-10, and KZ-2), those of the MTT structure type (for example, ZSM-23 and KZ-1), of the MFI structure type (for example, ZSM-5), of the MFS structure type (for example, ZSM-57), of the MEL-structure type (for example, ZSM-11), of the MTW structure type (for example, ZSM-12), of the EUO structure type (for example, EU-1) and members of the ferrierite family (for example, ZSM-35). In this specification, the term "structure type" is used in the sense described in the Structure Type Atlas, Zeolites 17, 1996.

Other examples of suitable molecular sieves include offretites, ZSM-4, erionites, chabazites, ZSM-18, zeolite beta, faujasites, zeolite L, mordenites and members of MCM-22 family of molecular sieves (including, for example, MCM-22, PSH-3, SSZ-25, ERB-1, ITQ-1, ITQ-2, MCM-36, MCM-49 and MCM-56).

The crystalline molecular sieve is advantageously ZSM-22 or ZSM-57. ZSM-22 and its manufacture are described in, for example, U.S. Pat. No. 4,556,477 and WO 93/25475, and ZSM-57 and its manufacture are described in, for example, EP-A-74,121 and U.S. Pat. No. 4,973,870, the disclosures of all of which are incorporated herein by reference. Mixtures of two or more molecular sieves e.g., a mixture of ZSM-22 and ZSM-57, may also be used. Preferably, the molecular sieve(s) is employed in its H— or acid form.

The molecular sieve conveniently has a crystallite size up to 5 μm, such as within the range of from 0.05 to 5 μm, for example from 0.05 to 2 μm, and typically from 0.1 to 1 μm. An as-synthesized molecular sieve is advantageously converted to its acid form, for example by acid treatment, e.g., by HCl, or by ammonium ion exchange, and subsequent calcination before use in the process of the invention. The calcined materials may be post-treated, such as by steaming. Although the invention will be described with reference to aluminosilicate zeolites, it is possible to use, as is known in the art, a material in which silicon and aluminium have been replaced in whole or in part by other elements, silicon more especially by germanium or phosphorus and aluminium more especially by boron, gallium, chromium and iron, materials containing such replacement lattice elements also being termed zeolites, and the term being used in the broader sense in this specification.

The molecular sieve may be supported or unsupported, for example in powder form, or used as an extrudate with an appropriate binder. Where a binder is employed, the binder is conveniently a metal oxide, such as alumina, and is present in an amount such that the oligomerization catalyst contains between about 2 and about 80 wt % of the molecular sieve.

Olefin Oligomerization Step

The reaction conditions used in the olefin oligomerization step of the present process are not narrowly defined. However, operating temperatures for the olefin oligomerization are generally between about 80° C. and about 350° C. Toward and above the upper end of the range, deoligomerization rates increase and may predominate over the oligomerization reaction, providing an upper limit to practical operation. More typically, the reaction temperature is in the range of about 130° C. to about 300° C., such as between about 135° C. and about 280° C., for example between about 160° C. and about 250° C.

The pressure is conveniently in the range of about 400 psig to about 4000 psig (2860 to 27680 Kpaa), such as from about 500 psig to about 1500 psig (3550 to 10440 kPaa). The olefin weight hourly space velocity is advantageously in the range of from about 0.1 hr$^{-1}$, to about 20 hr$^{-1}$, such as from about 0.5 hr$^{-1}$, to about 5 hr$^{-1}$.

Prior to introduction to the olefin oligomerization step, the feedstock may be hydrated and in particular sufficient water may be added to saturate the feedstock. Conveniently, the feedstock comprises from about 0.05 to about 0.25, such as from about 0.06 to about 0.20 and for example from about 0.10 to about 0.20, molar % water based on the total hydrocarbon content of the feedstock. If desired or required, the natural water content of the feedstock may be increased, for example, by passage through a thermostatted water saturator. Since the amount of water required to saturate the feedstock will depend upon the temperature and composition of the feedstock, control of the water content may be effected by appropriate control of the temperature of the feedstock.

The invention will now be more particularly described with reference to the following Examples.

EXAMPLE 1

A commercial propylene feed containing different sulfur compounds was processed over a sulfided NiMo/Al$_2$O$_3$ hydrotreating catalyst supplied by American Cyanamid as HDN-60. The processing was conducted at a presuure of 70 bar, a WHSV of 2 and at various temperatures as given in Table 1 below. A sulfur analysis of the feed was conducted by gas chromatography before and after the treatment and the results are summarized in Table 1. The results show the treatment resulted in a significant reduction in the concentration of mercaptans, dimethyl sulfide (DMS) and diethyl sulfide (DES) and a significant incease in the concentration of the propyl sulfide species.

TABLE 1

|  |  | Product, 10$^{-3}$ mol/l Temperature (° C.) | | |
|---|---|---|---|---|
| Component | Feed, 10$^{-3}$ mol/l | 180 | 220 | 240 |
| Dimethyl sulfide | 4.1 | 0.0 | 0.0 | 0.0 |
| N-propyl mercaptan | 9.8 | 0.2 | 0.4 | 0.6 |
| Thiophene + 2-butanethiol | 5.2 | 0.0 | 6.6 | 6.2 |
| Diethyl sulfide | 42.9 | 9.3 | 8.2 | 6.2 |
| N-butyl mercaptan | 2.9 | 0 | 0 | 0 |
| 3-methylthiophene | 2.3 | 2.4 | 2.2 | 1.6 |
| isopropyl sulfide | 10.4 | 34.7 | 40.0 | 29.8 |
| N-propyl-isopropyl sulfide | 3.2 | 27.3 | 39.0 | 29.3 |
| N-propylsulfide | 3.1 | 8.2 | 16.1 | 12.6 |
| Unknown | 6.7 | 0.0 | 0.0 | 0.0 |
| Total | 90.6 | 82.1 | 112.5 | 86.3 |

EXAMPLE 2

(Comparative)

40:1 SiO$_2$/Al$_2$O$_3$ H-ZSM-57 was mixed with alumina and extruded to form 50 wt % zeolite/50 wt % alumina catalyst extrudates. The catalyst was used to oligomerize an untreated C$_3$ hydrocarbon feedstock rich in propylene which was obtained from a commercial refinery and which had the following composition:

| Hydrocarbons, wt % | |
|---|---|
| ethane | 3.77 |
| ethene | 0.6 |
| propane | 18.54 |
| propene | 43.99 |
| iso-butane | 19.74 |
| n-butane | 10.72 |
| 1-butene | 0.36 |
| iso-butene | 0.62 |
| t-2-butene | 0.59 |
| c-2-butene | 0.35 |
| Oxygenates, wt ppm | |
| t-butyl alcohol | 8 |
| sec-butyl alcohol + methanol | 8 |
| iso-propyl alcohol | 97 |
| acetone | 135 |
| methyl ethyl ketone | 45 |
| Sulfur Compounds, wt ppm | |
| dimethyl sulfide | 0.6 |
| thiophene | 1 |
| propyl mercaptan | 1.3 |
| isobutyl mercaptan | 0.1 |
| diethyl sulfide | 6 |
| butyl mercaptan | 0.1 |
| dimethyl disulfide | 0.6 |
| tetrahydrothiophene | 1.1 |
| methylthiophenes | 0.8 |
| isopropyl sulfide | 1 |
| methyl ethyl sulfide | 0.3 |
| dimethyl thiophene | 0.3 |

The tests were conducted in pilot units, with the liquid feedstock being fed to the units using displacement pumps controlled by mass flow meters. The feedstock was saturated with water by passage upwardly through a vessel containing water at a constant 40° C. temperature. After exiting the hydrator the feed was pre-heated to the heater temperature and then passed downwards through a fixed-bed reactor equipped with an internal thermowell. The oligomerization reaction was conducted at temperatures of 130 to 300° C. and a pressure of 70 bar (7000 kPa) to ensure single phase conditions. The total feed WHSV was 2 and the olefin WHSV was 1. The reaction was exothermic leading to a non-isothermal temperature profile down the length of the catalyst bed.

No $C_2$— gases were fed or produced, and there was no evidence of any feedstock cracking. The product was cooled to near room temperature and the pressure was allowed to decrease to 20 bar (2000 kPa). Total reactor effluent samples were taken at 20 bar (2000 kPa) and were analyzed by GC. The feed and product olefin/paraffin ratios were compared in order to measure conversion. Liquid product was analyzed on a GC equipped with a platinum catalyst to hydrogenate product olefins to paraffins. Carbon number distribution and paraffin distribution were determined. Deactivation performance is shown in FIG. 1.

EXAMPLE 3

The process of Example 2 was repeated but with the $C_3$ hydrocarbon feedstock initially being passed over a nickel oxide catalyst at 6.7 WHSV (olefin WHSV 3.3) and a temperature of 170-250 ° C. and then subsequently being passed over the ZSM-57 catalyst again at 6.7 WHSV (olefin WHSV 3.3). Deactivation performance and unit conditions are provided in FIG. 1.

EXAMPLE 4

NiMo Co-Catalyst

The process of Example 2 was repeated but with the $C_3$ hydrocarbon feedstock initially being passed over a NiMo catalyst at 3 WHSV (olefin WHSV 1.5) and a temperature of 170-250° C. and then subsequently being passed over the ZSM-57 catalyst at 2 WHSV (olefin WHSV 1.0). Deactivation performance and unit conditions are provided in FIG. 1.

In reviewing FIG. 1, it is to be appreciated that light olefin oligomerization is typically conducted at a fixed feedrate and conversion. Freshly regenerated catalyst has the greatest activity. Because the desired feedrate is fixed, the reaction temperature is typically adjusted to maintain the target feedstock conversion. As the catalyst deactivates, the reaction temperature is raised to maintain constant conversion. This process is typically monitored by plotting the temperature required to achieve target conversion at the target WHSV against time. It is often desirable to track the stability of catalyst between and within runs where a variety of feedrates are utilized. To accomplish this, time is replaced by the cumulative amount of product produced by the catalyst expressed as weight units of product produced/wt unit of catalyst. In FIG. 1, the weight unit chosen is the ton, denoted as t in the drawing. The longer a reactor runs at constant conditions within the practical temperature range of the unit expressed either as days on stream or t product/t catalyst, the more stable the catalyst.

The data in FIG. 1 show that the experiments with the NiO and NiMo co-catalysts were more stable than the experiment with ZSM-57 extrudates alone. Lifetime is projected to at least triple due to the presence of the NiO co-catalyst, and to increase of the order of 10-fold when using the NiMo co-catalyst.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

We claim:

1. A process for oligomerizing an olefinic hydrocarbon feedstock comprising sulfur-containing molecules, the process comprising:
   (a) contacting the feedstock in the absence of hydrogen with a first metal oxide catalyst at a temperature of from about 180° C. to about 260° C. to convert at least a portion of said sulfur-containing molecules to larger sulfur-containing species, and then
   (b) contacting the feedstock under olefin oligomerization conditions with a second catalyst comprising a crystalline molecular sieve.

2. The process of claim 1 wherein the hydrocarbon feedstock comprises at least one olefin having about 2 to about 12 carbon atoms.

3. The process of claim 1 wherein the hydrocarbon feedstock comprises at least one olefin having about 2 to about 6 carbon atoms.

4. The process of claim 1 wherein the hydrocarbon feedstock comprises at least one olefin selected from propylene and/or butenes.

5. The process of claim 1 wherein the hydrocarbon feedstock comprises 0.1 to 10,000 ppm by volume of sulfur-containing molecules.

6. The process of claim 1 wherein the hydrocarbon feedstock comprises 1 to 100 ppm by volume of sulfur-containing molecules.

7. The process of claim 1 wherein the sulfur-containing molecules are selected from methyl mercaptan, ethyl mercaptan propyl mercaptan dimethyl sulfide, diethyl sulfide, ethyl methyl sulphide, n-propyl sulfide, 1- and 2-propane thiol. l-butane thiol and 1,1-methylethyl thiol, ethylmethyl disulphide, dimethyl disulphide and tetrahydrothiophene.

8. The process of claim 1 wherein the metal oxide of the first catalyst is selected from nickel oxide, molybdenum oxide, mixtures thereof and sulfided versions of nickel oxide and/or molybdenum oxide.

9. The process of claim 1 wherein (a) is conducted at conditions including a temperature ranging from about 180° C. to about 260° C. a weight hourly space velocity ranging from about 0.1 to about 100 $hr^{-1}$ and a pressure ranging from about 400 psig to about 4000 psig (2860 to 27680 Kpaa).

10. The process of claim 9 wherein the weight hourly space velocity ranges from about 0.5 to about 10 $hr^{-1}$ and the pressure ranges from about 500 psig to about 1500 psig (3550 to 10440 kPaa).

11. The process of claim 1 wherein the molecular sieve of the second catalyst is selected from molecular sieves of the TON, MTT, MFI, MFS, MEL, MTW and EUO structure type, members of the ferrierite family, members of the MCM-22 family, offretites, ZSM-4, erionites, chabazites, ZSM-18, zeolite beta, faujasites, zeolite L and mordenites.

12. The process of claim 1 wherein the molecular sieve of the second catalyst has the TON or MFS structure type.

13. The process of claim 1 wherein the molecular sieve of the second catalyst is ZSM-22 or ZSM-57.

14. The process of claim 1 wherein the feedstock is hydrated prior to contact with the second catalyst.

15. The process of claim 14 wherein the feedstock contacted with the second catalyst comprises from about 0.05 to about 0.25 molar % water based on the total hydrocarbon content of the feedstock.

16. The process of claim 14 wherein the feedstock contacted with the second catalyst comprises from about 0.06 to about 0.20 molar % water based on the total hydrocarbon content of the feedstock.

17. The process of claim 14 wherein the feedstock contacted with the second catalyst comprises from about 0.10 to about 0.20 molar % water based on the total hydrocarbon content of the feedstock.

18. The process of claim 1, wherein said first metal oxide catalyst is provided in a separate bed upstream from said second catalyst.

19. The process of claim 1, wherein said first metal oxide catalyst is provided in a separate reactor upstream from said second catalyst.

20. The process of claim 1, wherein said first metal oxide catalyst is provided as a top layer on said second catalyst.

21. The process of claim 1, wherein the second catalyst is ZSM-57.

22. The process of claim 1, wherein said feedstock is selected from an untreated refinery stream.

* * * * *